(12) United States Patent
Flagg (10) Patent No.: US 6,431,873 B1
(45) Date of Patent: Aug. 13, 2002

(54) FOOD GROUP MONITORING APPARATUS

(76) Inventor: Rodger H. Flagg, 7411 Gary St., Springfield, VA (US) 22150

( * ) Notice: Subject to any disclaimer, the term of this patent is extended or adjusted under 35 U.S.C. 154(b) by 55 days.

(21) Appl. No.: 09/725,206

(22) Filed: Nov. 29, 2000

(51) Int. Cl.[7] ............................................. G09B 19/00
(52) U.S. Cl. ...................... 434/127; 446/1; 434/430; 434/238; 434/370; 434/407
(58) Field of Search ................. 434/127; 273/156, 273/157 R, 153 R; 40/621; 30/114, 303; 294/7, 118; 100/234; 600/300; 446/1

(56) References Cited

U.S. PATENT DOCUMENTS

| | | | |
|---|---|---|---|
| D221,348 S | * | 8/1971 | Myer |
| 3,769,720 A | * | 11/1973 | Terrones |
| 4,672,478 A | * | 6/1987 | Perazzolo |
| 5,551,741 A | * | 9/1996 | Laboccetta |
| 5,640,774 A | * | 6/1997 | Goldman |
| 5,683,251 A | * | 11/1997 | Logan |
| 5,903,981 A | * | 5/1999 | Grow, II |

* cited by examiner

Primary Examiner—Jacob K. Ackun, Jr.
Assistant Examiner—Dmitry Suhol
(74) Attorney, Agent, or Firm—Rodger H. Flagg (57) ABSTRACT

A preprinted food group triangle sheet having indicia representative of a plurality of food groups thereon is sized to be inserted between a first triangular member and a second triangle member. A plurality of apertures extend in complimentary alignment through both the first and second triangular members. The plurality of apertures are positioned in relation to each of the food groups preprinted on a food group triangle sheet. One or more additional apertures may be provided to record the taking of vitamins, minerals or medication. A punch is provided for manual insertion into an aperture selected from a plurality of apertures. A flexible strap may be used to secure the punch to the food group monitoring apparatus. The food triangle sheets may be releasably secured in a pad, or on a page of a book, to provide a lasting record of the quantity and selection of foods consumed according to food groups, over time.

19 Claims, 5 Drawing Sheets

FOOD GROUP MONITORING APPARATUS

BACKGROUND OF THE INVENTION

On Apr. 28, 1992 the U.S. Department of Agriculture (USDA) published a food guide pyramid, for public use as a dietary aid to better control and monitor individual food consumption. The food guide pyramid disclosed three essential elements of a healthy diet: proportion, moderation, and variety. Diabetics are often taught to monitor the use of selected food groups to aid in regulating their dietary needs, and to better control their intake of fats, sodium and sugars. Likewise, a number of diet programs also use food group monitoring to aid in maintaining a healthy diet, and as a guide to controlled weight loss.

Typically, the base of the food pyramid is designated as the bread, cereal, rice and pasta group, hereinafter designated as the "A" food group, which is generally limited to six to eleven servings per day.

A vegetable group, hereinafter designated as the "B" food group, is generally positioned above the "A" food group on the food pyramid, and is often limited to three to five servings per day.

A fruit group, hereinafter designated as the "C" food group, is positioned adjacent to the "B" food group above the "A" food group. The "C" food group is typically limited to two to four servings per day.

A milk, yogurt & cheese group, hereinafter designated as the "D" food group, is typically located above the "B" food group, and is generally limited to two to three servings per day.

A meat, poultry, fish, dry beans, eggs and nut group, hereinafter designated as the "E" food group, is usually positioned above the "C" food group, adjacent to the "D" food group. The "E" food group is generally limited to two to three servings per day.

The tip of the pyramid is usually occupied by the fats, oils and sweets group, hereinafter designated as the "F" food group, which is to be used sparingly.

From time to time, the specified foods in a given food group may vary, according to changing dietary standards. For example, carbohydrate counters may group foods differently, by grouping various foods according to their carbohydrate content. Thus, the pyramid may be adapted to monitor food groups by carbohydrate content. Likewise, the food pyramid may also be adapted for use with a variety of special diet plans. Such modifications and adaptations are intended to fall within the scope of this disclosure and the accompanying claims.

User's of the food pyramid often find it difficult to reconstruct their food use patterns from meal to meal, and from day to day, for comparison over time. This is especially true of busy users who often dine at restaurants and fast food establishments, where they have only limited control of the quantity and selection of various food groups which accompany a selected main course.

It is at times recommended that users of the food pyramid write down their food selections in order to better monitor and control their food consumption patterns. This works best in a controlled environment, such as a home or hospital, where the user is in control of food selection and portion sizes, and works best where the meals are pre-planned in accordance with existing dietary standards.

U.S. Pat. No. 5,382,165 issuing to Jayne Knox on Jan. 17, 1995 discloses a pocket calorie counter using multiple, movable beads.

U.S. Pat. No. 3,841,260 issuing to Vance Sharp et. al on Oct. 15, 1974 discloses a diet management device with pins moved to tally the total calories in a 24 hour time period.

U.S. Pat. No. 3,195,813 issuing to J. H. Hart on Jul. 20, 1965 discloses a calorie counter using pins having at least three prong members, to lock the pins in any of a plurality of holes. The calorie counter adds calories to determine a total calorie count.

U.S. Pat. No. 4,828,498 issuing to Catherine Tilney on May 9, 1989 discloses a kit of color coded cards having self adhesive labels to match foods of the major food groups in a food exchange list.

U.S. Pat. No. 4,310,316 issuing to Patricia Thomann on Jan. 12, 1982 discloses a diet control apparatus which uses cards representing the food groups consumed during a 24 hour period.

U.S. Pat. No. 4,832,603 issuing to Jason Basil on May 23, 1989 discloses a diet control display board for diabetics with movable members representing respective food groups.

U.S. Pat. No. 4,606,555 issuing to Florence Adams on Aug. 19, 1986 discloses a diet control booklet having disposable tabs.

U.S. Pat. No. 788,713 issuing to C. Ellis on May 2, 1905 discloses a point counter for holding cards, which includes a hinged portion, and a plurality of perforations, used to keep score.

U.S. Pat. No. 2,011,722 issuing to H. Luhn on Aug. 20, 1935 discloses a recipe guide for mixed beverages, with cards held against a light source to read the combination of ingredients for a selected mixed drink.

U.S. Pat. No. 2,952,461 issuing to A. Boulanger on Sep. 13, 1960 is representative of prior art disclosing a travel game utilizing a plurality of pins on cords.

None of the known cited prior art discloses, nor makes obvious, the advantages of a portable, pocket sized, substantially triangular food group monitoring apparatus, utilizing first and second triangle members which are hinged or otherwise pivotally secured along their base portion, with a plurality of apertures positioned in alignment through the first and second triangle members, and with a punch having a shaft sized to be closely received in any selected one of the apertures.

The punch shaft is sized to penetrate and punch a hole in a triangular sheet placed between the first and second triangle portions of the food triangle, in order to record the quantity and selection of food groups consumed by the user over a specified period of time. Nor does the known prior art provide a convenient means to provide a lasting record of the quantity and selection of food groups consumed on a daily basis over time.

Therefore, what is needed is an easy and reliable way to identify and monitor the quantity and variety of a user's food consumption during the course of a day, particularly with reference to a balanced diet selected from a variety of food groups identified by the food pyramid, as recommended by the USDA, as well as by many dietitians and physicians.

Preferably the apparatus used to monitor food consumption should be inexpensive, portable, easy to use, and provide the user with a permanent record of each day's food group use over an extended period of time. The results may further be used as a periodic review by a user's physician or dietitian to monitor the user's food consumption over time. This is particularly important where food allergies may adversely affect a user's health and well being.

SUMMARY OF THE INVENTION

The food group monitoring apparatus disclosed herein, comprises a first triangular member and a second triangular member which are hingedly secured along their base portions, and sized to receive a food pyramid sheet therebetween. The first and second triangular members have a plurality of apertures which are aligned through both the first and second triangular members. The apertures are positioned in relation to each of the food groups preprinted on a food triangle sheet, and the quantity of apertures in relation to the food groups is preferably representative of the maximum recommended consumption of each food group during a specified period of time, such as one day.

One or more additional apertures may be provided to record the taking of medication and/or vitamins. A punch is provided for manual insertion into any selected aperture, and the punch is used to punch a hole through the food triangle sheet located between the first and second triangular members, for each portion of a selected food group consumed in a day. The food triangle sheets may be initially supplied in the form of a pad or book for periodic removal therefrom. The food triangle sheets are preferably preprinted, precut and releasably secured into a pad or book for easy access. The punched food triangle sheets are preferably stored in a book, binder or envelope after use, providing a lasting record of the quantity and selection of foods according to the consumption of selected food groups by the user, over time.

DESCRIPTION OF THE DRAWINGS

The above mentioned and other features and objects of this invention and the manner of attaining them will become more apparent and the invention itself will be best understood by reference to the following description of the invention, when considered in conjunction with the accompanying drawings, wherein.

DESCRIPTION OF THE PREFERRED EMBODIMENT

The food group monitoring apparatus 10 disclosed in FIG. 1 through FIG. 9, is shaped in a generally triangular configuration to conform to the shape of a typical food pyramid, illustrating a plurality of food groups 14, generally designated "A" through "F". The food triangle 12 preferably incorporates the food groups 14 used on the food pyramid recommended by the U.S.D.A, and reproduced for use on a large quantity of consumer food related products, such as cereal boxes, health food, etc. A copy of one such use is incorporated by reference herein, as exhibit "A".

Figures 1, 2:
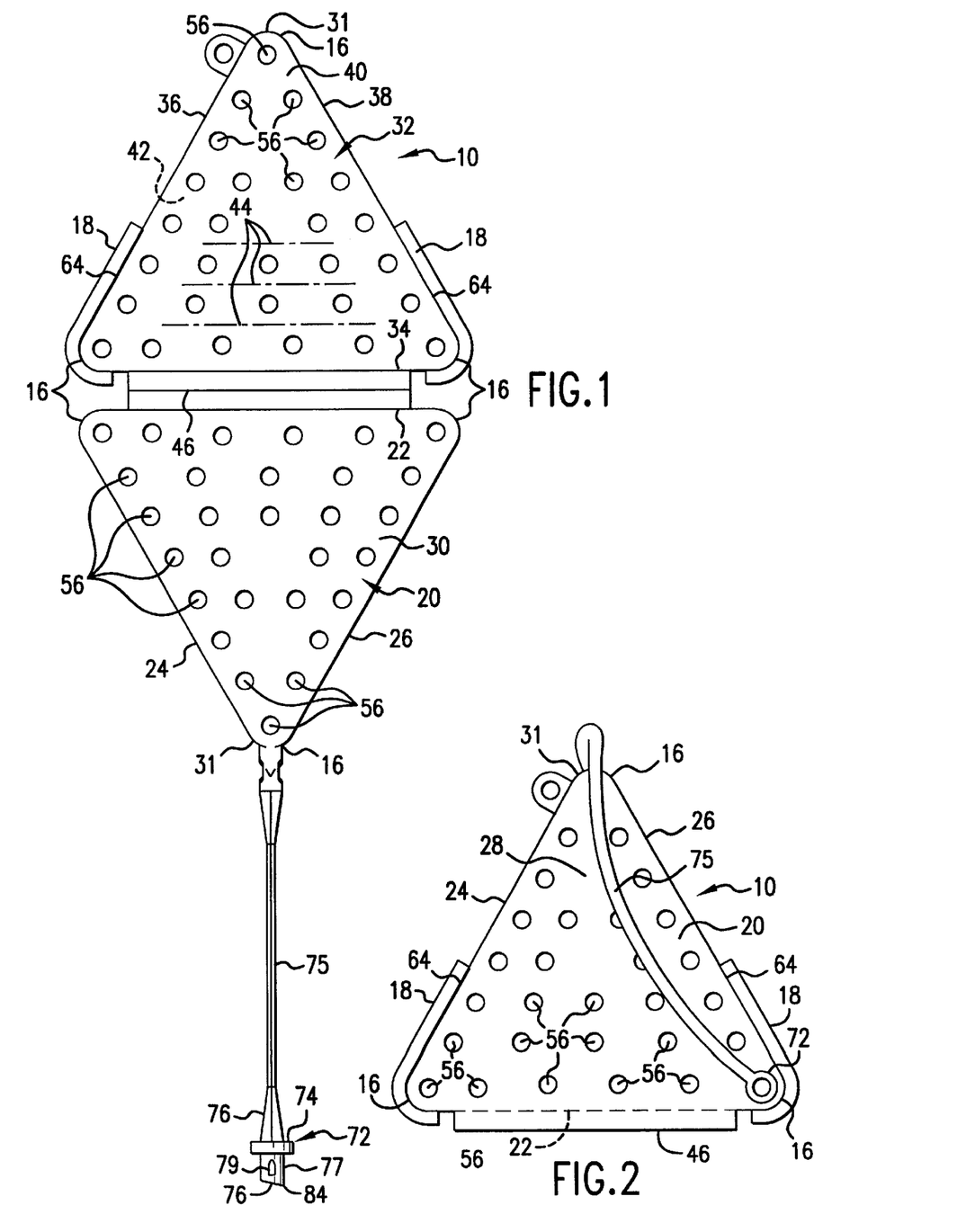
FIG. 1 is a top view of the food group monitoring apparatus, shown in an opened position, and wherein the punch is connected to the food monitoring apparatus with a suitable flexible member, such as a cord or strap.
FIG. 2 is a top view of the food group monitoring apparatus shown with the first and second triangle members in a closed position, with the punch inserted into one of the apertures provided.

The food group monitoring apparatus 10 shown in FIG. 1 and FIG. 2 comprises a first triangle member 20, having a base portion 22, a left side portion 24, a right side portion 26, a front planar surface 28, and a back planar surface 30. The first triangle member 20 is preferably transparent. Alternately, the first triangle member 20 may be translucent to suit manufacturing or design preference.

A second triangle member 32 may be transparent, translucent or opaque to suit manufacturing or design preference. If the second triangle member 32 is transparent, the back planar surface 42 of the second triangle member 32 may be marked with indicia 44, such as a trademark, manufacturing address, pattern, design, letters or numbers, or combination thereof, to differentiate the first triangle member 20 from the second triangle member 32. The second triangle member 32 is substantially similar in size to the first triangle member 20. The second triangle member 32 also has a base portion 34, a left side portion 36, a right side portion 38, a front planar surface 40 and a back planar surface 42. The first and second planar triangle members 20, 32 may be made of any suitable material, such as plastic, glass or other known transparent or translucent material to suit manufacturing or design preference.

The corners of the first triangle member 20 are each preferably rounded or curved 16 to eliminate sharp corners at the acute angles where the left side portion 24, the right side portion 26, and the base portion 22 each converge. Likewise, the corners of the second triangle member 32 are also preferably rounded or curved 16 to eliminate sharp corners at the acute angles where the left side portion 36, the right side portion 38 and the base portion 34 each converge.

A raised ridge portion 18 may extend at least partially along the left and right sides of the second triangle member 32, to aid in aligning the triangular sheet material 48 within the raised ridge portion 18, and may further serve as a catch means 64 to releasably secure the first and second triangle members 20, 32 together in a closed position 68.

Figure 9:
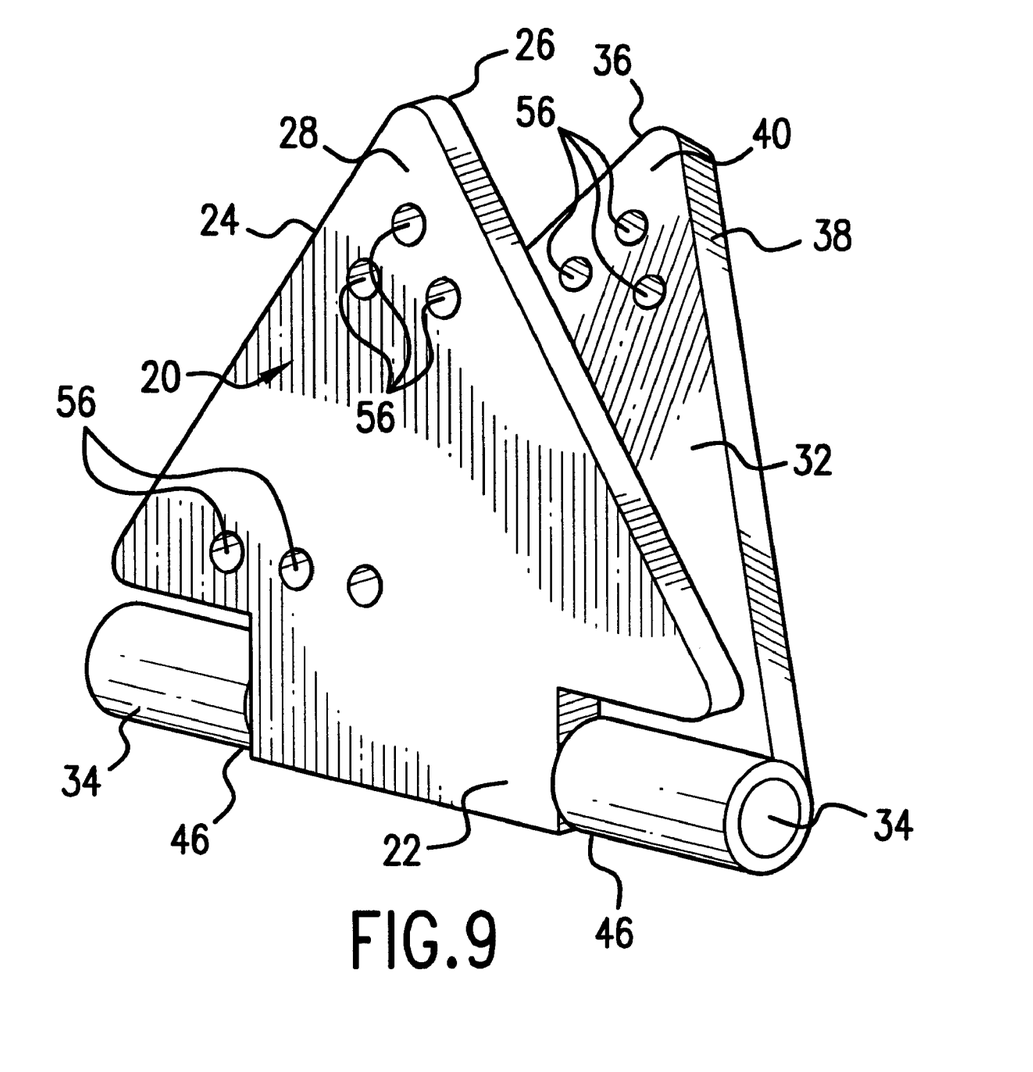
FIG. 9 is an alternate embodiment of a hinge means, in the form of a pivotally secured food group monitoring apparatus, shown partially opened.

The base portion 34 of the second triangle member 32 is connected by a hinge means 46 to the base portion 22 of the first triangle member 20, to enable the user to selectively open and close the first triangle member 20 in relation to the second triangle member 32. This may be accomplished with a continuous hinge means 46 molded between the first triangle member 20 and the second triangle member 32. Alternately, any known hinge means 46 may be used. The hinge means 46 may be in the form of a suitable pivot means, as shown in FIG. 9.

The hinge means 46 is preferably in the form of a "living hinge" extending between the base portions 22,36 of the first and second triangle members 20,32, as shown in FIG. 1 and FIG. 2. Alternately, any known hinge means 46 may be used, to suit manufacturing or design preference.

As shown in FIG. 1, the hinge means 46 enables the first and second triangle members 20, 32 to be selectively opened into an open position 66 to insert a preprinted triangular sheet material 48, such as paper or thin plastic film, between the back planar surface 30 of the first triangle member 20 and the front planar surface 40 of the second triangle member 32.

The preprinted triangular sheet material 48 has food indicia 50 on at least one side thereon representing the various food groups 14 on the food triangle 12, which may be viewed by the user through the first transparent or translucent triangle 20, during use. Once used, the food triangle 12 is preferably stored for later review by the user, the user's physician, or the user's dietitian to determine the user's food use patterns over time.

Alternately, the food indicia 50 representing the food groups 14 may be adapted for a custom diet regimen, or to enable the user to monitor carbohydrate consumption, calories, etc.

The circular dots typically used to signify fats, and the triangular dots used to signify sugars, (not shown), on the conventional food pyramid disclosed by the USDA, may optionally be eliminated from the food indicia 50 on the preprinted triangular sheet material 48, representative of a food triangle 12, disclosed herein. Likewise, the partial side view of the conventional food pyramid may also be eliminated, when used with this food group monitoring apparatus 10.

Where both the first and second triangle members 20, 32 are transparent or translucent, and where the plurality of apertures 56 for the food triangle 12 are symmetrically positioned, the food indicia 50 on the triangular sheet material 48 representing the food groups 14 on the food pyramid 12 may be viewed through either the first or second transparent triangle members 20, 32, eliminating the need to differentiate between the first and second triangle members 20, 32.

Where the plurality of apertures 56 are not symmetrically positioned, the food indicia 50 on the preprinted triangular sheet material 48, representing selected food groups 14 is preferably viewed through the first triangle member 20. The second triangle member 32 may therefore be colored, translucent or opaque, incorporate a raised ridge portion, or otherwise be marked with indicia 44 to differentiate the first triangle member 20 from the second triangle member 32. The first triangle member 20 and the second triangle member 32 may be molded of a suitable plastic material together with an integral hinge means 46 as a single molded apparatus, as shown in FIG. 1. One such suitable material is clarified polypropylene, which is adaptable for molding a continuos hinge means 46 between the base portions of the first and second triangles 20, 32.

Alternately, the first and second triangle members 20, 32 may be separately formed, shaped or cut from suitable planar sheet material and connected together by a suitable hinge means 46 at assembly.

A hinge means 46 may alternately be in the form of a pivot means, to selectively move the first triangle member 20 in relation to the second triangle member 32 between an open position 66 and a closed position 68. One such hinge means 47 is shown in FIG. 9.

A plurality of apertures 56 extend in adjacent alignment through both the first and second triangle members 20, 32, when the first and second triangle members 20, 32 are folded together in a closed position 68 about the hinge means 46. The plurality of apertures 56 are positioned in the first triangle member 20 to align with food indicia 50 of each food group 14 preprinted on the triangular sheet material 48, when the preprinted triangular sheet material 48 is inserted between the first and second triangle members 20, 32. The food indicia 50 on the preprinted triangle sheet material 48 is preferably positioned for viewing through the first triangle member 20. The plurality of apertures 56 in the first and second triangle members 20, 32 are positioned in relation to the food indicia 50 representative of each food group 14 displayed on the preprinted triangular sheet material 48.

While the quantity of apertures 56 positioned in relation to a selected food group 14 may vary from user to user, according to their diet, nutritional requirements, or medical history, the selected quantity of apertures 56 in each food group 14 are preferably selected to be the maximum recommended quantity of serving portions for each food group displayed on the preprinted triangular sheet material 48, over a specified time, such as a day.

The plurality of apertures 56 may be molded into the first and second triangle members 20, 32, or the apertures 56 may alternately be drilled, punched or otherwise formed into aligned apertures through the first and second triangle members 20, 32, to suit design or manufacturing preference.

The thickness of the preprinted triangular sheet material 48 is selected to ensure penetration of the punch means 72 shaft portion 76 through the preprinted triangular sheet material 48, when the top portion 74 of the punch means 72 is manually pressed into a selected aperture 56 by a moderate user effort. By way of an example embodiment, a paper representative of 20 pound copy paper has been found to provide excellent results, when penetrated by a one-eighth inch diameter shaft 76. Of course, other paper weight and other shaft diameters may be used, without departing from this disclosure, or the scope of the following claims.

Figure 3:
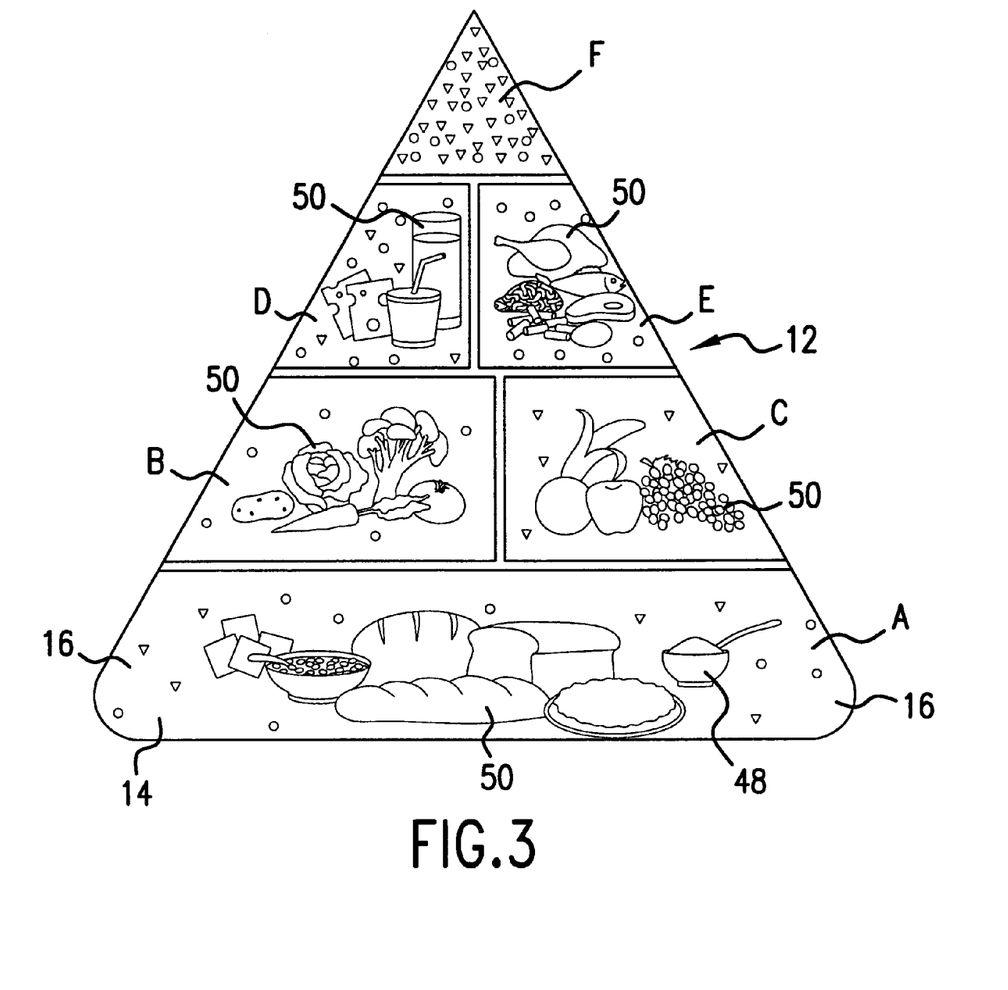
FIG. 3 is a front view of a preprinted and precut triangular sheet material.

The preprinted triangular sheet material 48 shown in FIG. 3 is positioned between the first and second triangles 20, 32, with the base of the food pyramid 12 positioned adjacent to the base portion 22 of the first pyramid 20. This serves to align the selected food groups 14 in relation to a selected quantity of apertures 56, which are preferably positioned as disclosed herein.

As shown in FIG. 1, eleven apertures 56 are preferably positioned in alignment with the food group "A"; five apertures 56 are preferably positioned in alignment with the food group "B"; four apertures 56 are preferably positioned in alignment with the food group "C"; three apertures 56 are preferably positioned in alignment with the food group "D"; three apertures 56 are preferably positioned in alignment with the food group "E"; and at least one aperture 56 is positioned in proximity to the tip of the food triangle 12, in alignment with the food group "F". One or more aperture(s) 56 may be used to store and transport a punch means 72 therein between use.

At least one medication aperture 56 may also be positioned in proximity to the tip portion 31 of the food triangle 12 in alignment with the food group "F". The medication aperture(s) 56 may be used to record the taking of medication, which is not a part of a conventional food pyramid 12, but has been found to be extremely useful to the user of the food group monitoring apparatus 10, who requires daily medication. Alternately, at least one aperture 56 may also be used to record the taking of vitamins or minerals, etc.

An optional flexible strap, cord, chain or other known flexible attachment means 75 may be positioned at any convenient location on the first or second triangle members 20, 32, or in relation to the hinge means 46, for ease in releasably securing the food group monitoring apparatus 10 to a user's wearing apparel, such as a belt, belt loop, garment, handbag, key chain, etc. (not shown), without departing from this disclosure, or the scope of the following claims. The flexible attachment means 75 is preferably sized to be wrapped around the selected portion of the user's wearing apparel, and releasably secured thereto by inserting the punch means 72 into a selected aperture 56 extending through the first and second triangle members 20, 32.

The flexible attachment means 75 may be adapted to be molded together with the first and second triangular members 20, 32, and a punch means 72 may also be molded or otherwise incorporated into the flexible attachment means 75 near the distal end 76 of the flexible attachment means 75, as shown in FIG. 1.

Preferably, the food group monitoring apparatus 10 is sized to fit easily into a user's hand, pocket or purse. Thus, the preferred size of the first triangle member 20 is selected to be from one inch to four and one-half inches in length along the base portion 22 of the first triangle member 20, with the left and right sides 24, 26 of the first triangle member 20 preferably symmetrically aligned, and sized to be selected from a range of plus or minus 30 percent of the length of the base portion 22.

Other sizes may be alternately selected, where portability in a user's pocket is not desired. For example, an enlarged food group monitoring apparatus 10 may be hung on a wall or propped upon a table for use as a teaching aid, to instruct a group in the most beneficial use of the food group monitoring apparatus 10. Thus, while the preferred size is specified herein, other sizes may also be used, and such use is intended to fall within the scope of this disclosure, and the following claims.

Figure 6:
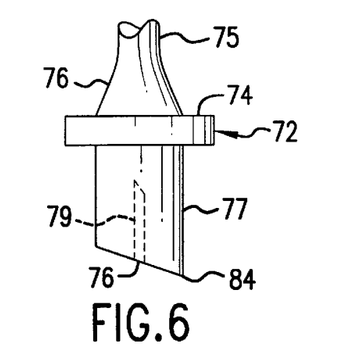
FIG. 6 is a side view of a punch showing a tapered end portion.

As shown in FIG. 6, a manually positioned punch means 72 having an enlarged top portion 74 and an elongated shaft portion 77 is used to selectively punch holes 78 in the preprinted triangular sheet material 48 to designate the consumption of a predetermined quantity of food in a selected food group 14. The shaft portion 77 of the punch means 72 is inserted and closely received into a selected aperture 56, and pushed through the triangular sheet material 48 positioned between the first and second triangles 20, 32, leaving a punched hole 78 in the preprinted triangular sheet material 48 in proximity to a selected food indicia 50 located on the preprinted triangular sheet material 48.

The top portion 74 of the punch means 72 is preferably larger than the shaft portion 77, to limit the length of penetration of the shaft portion 77, and for ease of manually grasping the punch means 72. The shaft portion 77 is preferably sized to penetrate through a selected aperture 56 in the first triangle 20, and to extend through the preprinted triangular sheet material 48, into the aligned aperture 56 in the second triangle 32. Penetration of the punch means 72 shaft portion 77 through the preprinted triangular sheet material 48, provides an audible sound and a tactile feel, which confirms to the user that a punched hole 78 has been made by the punch means 72 in the selected aperture 56.

Preferably, the shaft portion 77 of the punch means 72 extends through the back planar surface 44 of the second triangle member 32, to ensure that a clean hole has been punched through the triangular sheet material 48. The distal end 76 of the shaft 77 is preferably slightly tapered, slotted or flared 80, to provide a limited resistance to removal of the punch means 72 from the selected aperture 56, so that the punch means 72 will not be misplaced or become lost during transport or handling.

The plurality of apertures 56 in the second triangle member 32 may be concentrically tapered 82 to correspond with the flared end portion 84 of the punch shaft 77. The resistance of the flared end portion 84 of punch shaft portion 77 is designed to be easily overcome as the user pulls on the top portion 74 of punch means 72 while holding onto the triangular portions 20, 32. Thus, the user may easily reposition the punch means 72 in relation to another selected aperture 56 among the plurality of apertures 56 located in the first triangle member 20, as selected quantities of food portions are consumed.

Alternately, the raised ridge portion 18 shown in FIG. 1 may serve to bias the first triangular member 20 in relation to the second triangular member 32, to provide some resistance to removal of the punch shaft 76 from the selected aperture 56.

One or more slots or grooves 79 may extend along at least a portion of the flared end portion 84 of the punch means 72, to aid in providing the desired flexibility to reduce the resistance required to manually insert and withdraw the punch means 72 from any one of the plurality of apertures 56.

The flared end portion 84 of the punch shaft 77 is preferably tapered in proximity to the distal end 76, to a diameter slightly less than the diameter of the apertures 56 in the first triangle member 20, for ease of insertion of the punch means 72 into a selected aperture 56.

The punched holes 78 in the food triangle 12 are easily viewed by the user in preparation for selection of subsequent food identified by each of the food groups 14. A user with poor vision may readily identify each punched hole 78 by holding the front planar surface 28 of the food group monitoring apparatus 10 towards a light source (not shown). The light will shine through the punched holes 78, providing a reliable and easily viewable record of the food groups 14 consumed by the user, during a specified period of time, such as a day.

Figure 7:
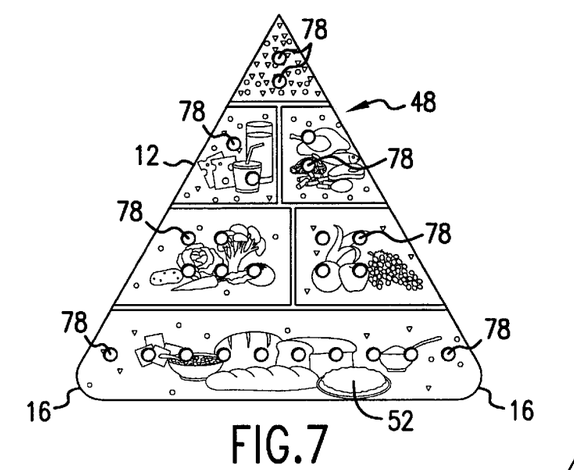
FIG. 7 is a front view of a punched triangle sheet, having a plurality of punched holes therein, showing a user's food consumption according to food groups, over a period of one day.

As shown in FIG. 7, the punched hole(s) 78 extend through selected food groups 14 on the food triangle 12 located on the preprinted triangular sheet material 48 to provide a lasting record of the quantity of food groups 14 consumed on a given day, enabling the user to readily recall and intelligently select a balanced and organized diet based upon the food groups 14 located on the food triangle 12.

This is especially important where the user eats out, and cannot entirely control the type of food provided with a main course selection.

A flexible attachment means 75 may be secured at one end to the punch means 72, and at the opposite end to at least one of the first and second triangle members 20, 32, or to the hinge means 46. The flexible attachment means 75 ensures that the punch means 72 will not easily become lost or misplaced during use, handling or transport of the food group monitoring apparatus 10.

The flexible attachment means 75 may also be used to secure the food group monitoring apparatus 10 to a user's belt, belt loop, key chain, pocketbook, pocket, wearing apparel, book or binder, etc. The flexible attachment means 75 may be secured to one of the first triangle member 20, the second triangle member 32 or the hinge means 46, to suit manufacturing and design preference. Any conventional flexible attachment means 75 may be used, such as a strap, cord, key chain, string, yarn, etc. without departing from the scope of this disclosure, or from the following claims.

Food indicia 50 representing each of the selected food groups 14 on the food pyramid 12 is preferably pre-printed or otherwise illustrated in multiple colors upon suitable triangular sheet material 48, for ease of visually identifying each of the food groups 14 in the food pyramid 12.

The preprinted triangular sheet material 48 is preferably precut into a desired triangular shape shown in FIG. 3, which is substantially equal to slightly smaller than the size and shape of the first and second triangle members 20, 32.

Figure 5:
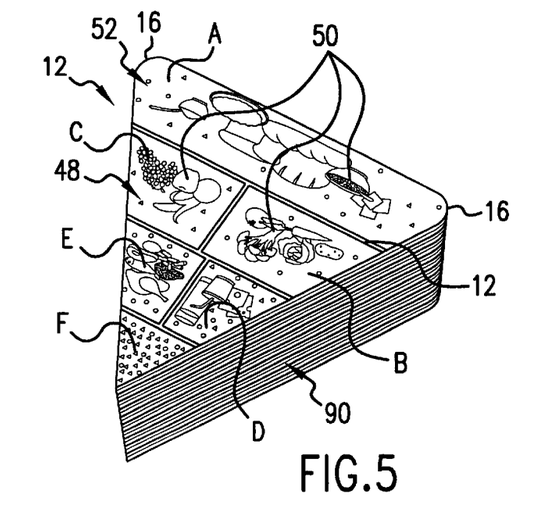
FIG. 5 is a perspective view of a triangular pad, having a plurality of food triangles arranged for sequential removal therefrom.

A plurality of preprinted triangular sheet material 48 may be prepackaged into a triangular pad 90 of food triangles 12, with peelable adhesive 92 on at least a portion of the back side 54 of the preprinted triangular sheet material 48, as shown in FIG. 5. The food triangles 12 may then be sequentially removed from the pad 90 as needed for insertion between the first and second triangles 20, 32, in preparation for each day's use.

At the end of a predetermined time period, such as a day, the punched triangular sheet material 48, representative of a conventional food pyramid 12, is removed from between the first and second triangles 20, 32. The punched triangular sheet material 48 may then be conveniently stored in a suitable book 94 for future reference. The book 94 may be in the form of a book, binder, folder, container, envelope, etc., hereinafter referred to as a book 94.

Thus, a record of food group 14 consumption may be established over a selected period of time, such as a week, month or year, for periodic reference by the user, and the user's doctor, or dietitian. Such a record is useful to establish food pattern behavior, and for comparison with other data, such as blood glucose monitoring, weight gain or loss, medication compliance, diet, exercise, allergies, etc. Comparison of daily results from food pattern monitoring will enable the user to constructively monitor their food pattern behavior over time and to adjust or modify their food consumption pattern usage to achieve the desired results.

The food triangle sheets 12 are preferably, alternately stored in a book 94 which may also include printed material representing detailed instructions on the use of selected food groups 14 identified by the food triangle sheet 12. To save space, the preprinted triangular sheet material 48 is preferably alternately positioned on a page 96 of the book 94, as shown in FIG. 4A, FIG. 4B and FIG. 4c.

Figure 8:
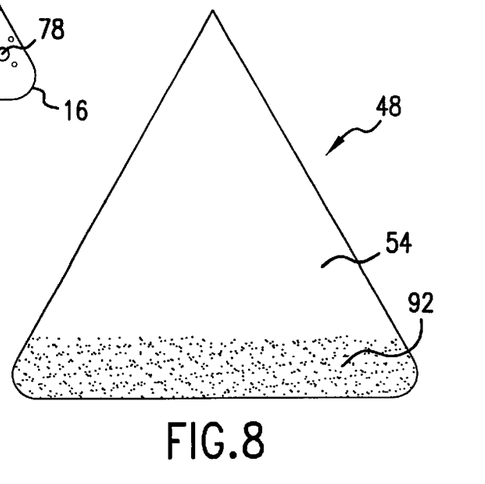
FIG. 8 is a back side view of a food triangle, showing peelable adhesive located on a portion of the back side.

Preferably, each food triangular sheet 12 preprinted on suitable triangular sheet material 48 is releasably secured to a page 96 in the book 94 with a suitable peelable adhesive 92 located on the back side 54 of the preprinted triangular sheet material 48, in a manner well known in the art to provide a peelable food pyramid 12, similar to a sticker or "post-it" type notepad. The peelable adhesive may be uniformly distributed upon the back side 54 of the triangular sheet material 48, or may be placed upon a portion of the back side 54, as shown in FIG. 8. The preprinted triangular sheet material 48 may be stored after use upon a suitable page 96 in a book 94, for future reference.

The pages 96 used to store the punched food pyramids 12 preprinted on triangular sheet material 48 may be grouped into a book 94 or log, according to a specific time period, such as a week, a month, or a year. Multiple books 94 with unused food pyramids 12 may be provided, for long term monitoring, and additional food pyramids 12 and books 94 may be purchased separately to extend the use of the food group monitoring apparatus 10 for additional time periods, such as a month, three months, or a year.

Figure 4A:
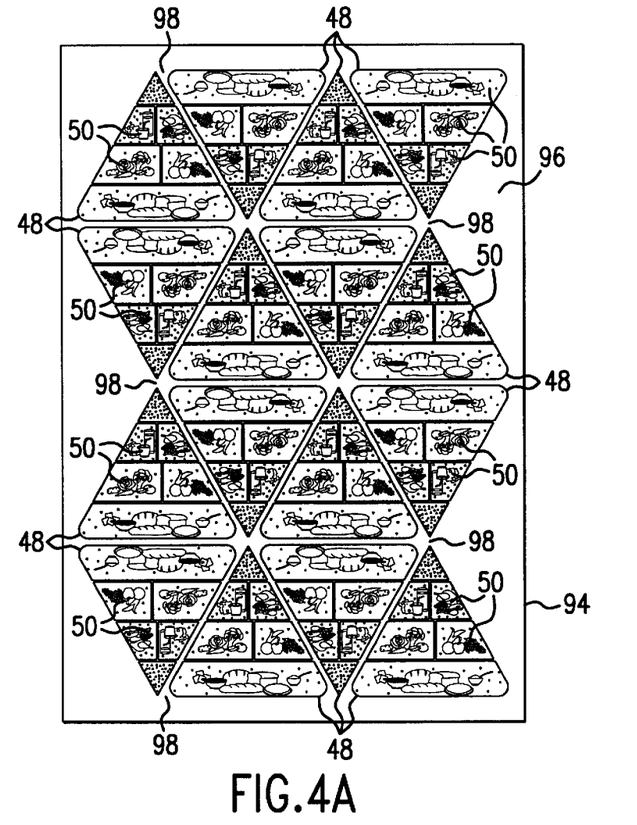
FIG. 4A is a plan view of sixteen food triangles arranged upon a page, wherein one back-to-back page contains enough food triangles to last a month.
Figure 4B:
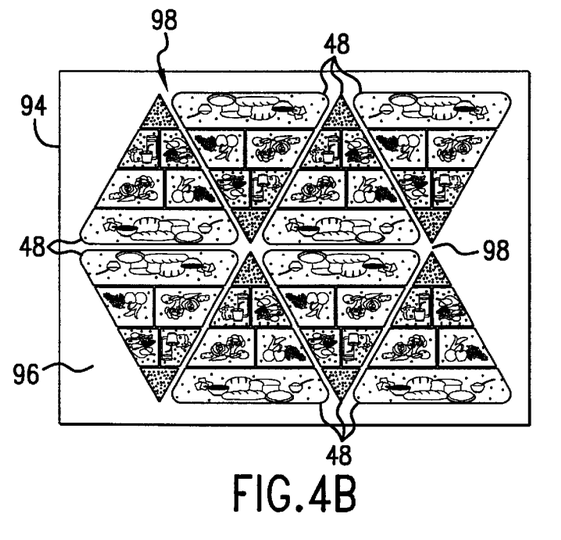
FIG. 4B is a plan view of eight food triangles arranged upon a page, with two back-to-back pages containing enough food triangles to last for a month.
Figure 4C:
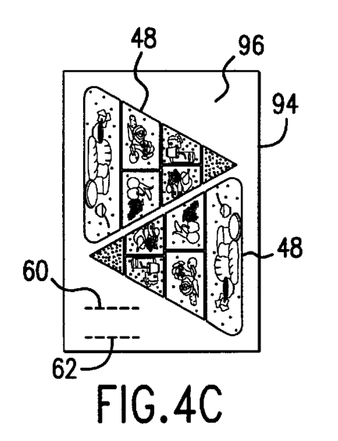
FIG. 4C is a plan view of two food triangles arranged upon a page, with eight back-to-back pages containing enough food triangles to last for a month.

For example, 16 food pyramids 12, each having sides of about three inches each, will fit on a conventional 8 and ½ inch by 11 inch page 96 by alternately positioning 98 the preprinted food pyramids sheets 12 into four rows of four preprinted triangular sheet material 48 per row, as shown in FIG. 4A. Thus, one double sided page 96 of precut food pyramids 12 would provide enough food pyramids 12 preprinted on triangular sheet material 48 to last for a month, with at least one food pyramid 12 to spare.

Alternately, as shown in FIG. 4B, eight food triangle sheets 12, each having equal sides of two inches each, will fit on a conventional 5 inch by 7 inch page 96, by alternately positioning 98 the preprinted food triangular sheets 12 into two rows of four preprinted food triangle sheets 12 per row. Thus, two double sided pages 96 of precut food pyramids 12 would provide more than enough food pyramids 12 to last for a month.

A month's supply of two inch wide food pyramids 12 preprinted on suitable triangular sheet material 48 may be stored two per page in a pocket sized book 94 or booklet measuring 2½ by 4½ inches, as shown in FIG. 4C. This size would enable the user to easily carry the book 94 in a shirt-pocket, jacket or purse.

Where both sides of the page 96 are used to store two triangular food pyramids 12 each, an entire month's supply could be stored on eight pages 96 sized to hold two triangular food pyramids 12 preprinted on triangular sheet material. Separate books 94 may thus be used for each month of use, enabling the user to start using the books 94 during any month of the year. The date 60 (day, month & year) may be preprinted on each page adjacent to each food triangle sheet 12, or may alternately be written on the sheet by the user at the time of use. The time-of-use 62 may also be recorded.

The pages 96 are preferably sized to receive from one to thirty-two triangles 12 per page, with triangles 12 positioned on either one side or both sides of each page 96.

These sizes are intended to be representative of preferred embodiments, and one skilled in this art may select other sizes without departing from the teachings of this disclosure, or from the scope of the following claims.

Where a book 94 is used, additional pages 96 may be provided with suitable book indicia (not shown) disclosing detailed instructions in the use of the food groups 14 designated upon the food triangle sheets 12. This will aid the user in achieving the desired results.

The book 94 may also include instructions in the use of the food group monitoring apparatus 10, disclosed herein. Additional book indicia (not shown) may also be included, such as sample recipes, special instructions for diabetics, dieting, medication and exercise instructions, recommended foods within a selected food group, etc.

A suitable catch means 64 may be used to keep the first and second triangle members 20, 32 in a closed position during use. The catch means 64 is designed to release the first triangle member 20 from the second triangle member 32, when the first and second triangle members 20, 32 are moved from a closed position to an open position by the user, in preparation for insertion of the food triangle 12 between the back planar surface 30 of the first triangle member 20 and the front planar surface 42 of the second triangle member 32.

Where a raised ridge 18 is provided along at least a portion of at least one of the left and right sides 36, 38 of the second triangle 32, the raised ridge 18 may also serve as the catch means 64. Any conventional catch means 64 may alternately be used without departing from the scope of this disclosure, and the accompanying claims.

The date-of-use 60 and time-of-use 62 may be marked at the time of use upon each food pyramid 12, for ease of sequentially organizing the food triangle sheets 12 according to an extended period of time, such as a week, month or year. Alternately, the date-of-use 60 may be preprinted upon each food pyramid 12, or incorporated onto the page 96 on which the food pyramids 12 are stored in the book 94.

The preprinted triangular sheet material 48 need not have peelable adhesive 92 thereon. The preprinted triangular sheet material 48 may be stored in a suitable envelope or other enclosure (not shown) before and after use.

Thus, while the preferred embodiment of the food group monitoring apparatus 10 has been disclosed herein, and shown in FIGS. 1 through 9, numerous modifications and adaptations may be made by one of average skill in this art, and such modifications and adaptations are intended to fall within the scope of this disclosure, and the following claims.

What is claimed is:

1. A food group monitoring apparatus, comprising:
    a) a first triangle member having a base portion, a left side portion, a right side portion, a front planar surface and a back planar surface, the first triangle member selected to be one of a transparent or translucent material;
    b) a second triangle member having a base portion, a left side portion, a right side portion, a front planar surface and a back planar surface, with the back planer surface of the first triangle member adjacent to the front planar surface of the second triangle member;
    c) the base portion of the first triangle member connected by a hinge means to the base portion of the second triangle member;
    d) a preprinted triangular sheet material sized to be received between the first triangle member and the second triangle member when the first and second triangle members are opened about the hinged means, the preprinted triangular sheet material having indicia thereon representative of a plurality of food groups;
    e) a plurality of apertures extending in complimentary alignment through the first triangle member and the second triangle member when the first and second triangle members are placed in a closed position about the hinged portion, the plurality of apertures further positioned in alignment with indicia on the preprinted triangular sheet material;
    f) a manually manipulated punch means having a shaft sized to be closely received within any selected one of the plurality of apertures, the punch means having a shaft of a length to selectively punch a hole in the preprinted triangular sheet material when the punch means is pushed through an aperture selected from the plurality of apertures located in the first triangle member.

2. The food group monitoring apparatus of claim 1, wherein the quantity of apertures positioned in relation to each food group preprinted on the triangular sheet material is representative of the recommended maximum quantity of food portions recommended for consumption from each food group during a predetermined time period.

3. The food group monitoring apparatus of claim 1, wherein the punch means further includes shaft sized to be closely received in a selected aperture, the punch means having a head portion sized to be larger than the shaft, for limiting penetration of the punch means through the first and second triangle members, the head portion further sized to be grasped by a user for ease of manual manipulation of the punch means into any selected aperture among the plurality of apertures located in the first and second triangle members.

4. The food group monitoring apparatus of claim 1, wherein the punch means has a shaft with an inclined distal end, and the shaft is sized to penetrate through a selected aperture in the first triangular member, through the preprinted triangular sheet material positioned between the first triangular member and the second triangle member; said punch means shaft further sized to extend at least partially through the aligned aperture in the second triangular member in order to punch a hole in the preprinted triangular sheet material.

5. The food group monitoring apparatus of claim 3, wherein a flexible strap has a first end and a distal end; the first end of the flexible strap is secured to one of the first triangle member, the second triangle member, and the hinge means; the flexible strap of a length sufficient to place the distal end of said flexible strap in alignment with any selected one of the plurality of apertures in the first triangle member, with a punch means secured to said flexible strap in proximity to the distal end of the flexible strap.

6. The food group monitoring apparatus of claim 1, wherein the first triangle member, the second triangle member, the hinge means, the flexible strap, and the punch means are molded as a single unit from a suitable plastic material.

7. The food group monitoring apparatus of claim 1, wherein the preprinted triangular sheet material are releasably secured together with a peelable adhesive into a substantially triangular pad having a plurality of food triangles aligned together for sequential removal therefrom.

8. The food group monitoring apparatus of claim 1, wherein a plurality of the food triangle sheets are assembled onto at least one page in a book, with adjacent food triangles alternately rotated to more compactly position the plurality food triangles on said page of said book.

9. The food group monitoring apparatus of claim 1, wherein one of the food groups on the preprinted triangular sheet material is an "A" food group, with eleven apertures extending through the first and second triangle members when positioned in alignment with the "A" food group; one of the food groups on the preprinted triangular sheet material is a "B" food group, with five apertures extending through the first and second triangle members when positioned in alignment with the "B" food group; one of the food groups on the preprinted triangular sheet material is a "C" food group, with four apertures extending through the first and second triangle members when positioned in alignment with the "C" food group; one of the food groups on the preprinted triangular sheet material is a "D" food group, with three apertures extending through the first and second triangle members when positioned in alignment with the "D" food group; one of the food groups on the preprinted triangular sheet material is an "E" food group, with three apertures extending through the first and second triangle members when positioned in alignment with the "E" food group; one of the food groups on the preprinted triangular sheet material is an "F" food group, with at least one aperture extending through the first and second triangle members when positioned in alignment with the "F" food group, and wherein at least one aperture is used to record the taking of medication during a selected time period.

10. The food group monitoring apparatus of claim 1, wherein the first triangle member has a base portion sized to be from one inch to four and one-half inches in length, with the left and right sides of the first triangle member symmetrically aligned and sized to be selected from a range of plus or minus 30 percent of the length of the base portion.

11. The food group monitoring apparatus of claim 1, wherein the first triangle member is made of a clarified translucent plastic material.

12. The food group monitoring apparatus of claim 1, wherein the hinge means comprises a snap together pivotal assembly, with the first triangle member having a first protrusion and a first detent in opposing alignment with the first protrusion; and the second triangle member having a second protrusion and a second detent in opposing alignment with the second protrusion; the first protrusion in the first triangle member sized to be rotatably received in the second detent in the second triangle member, and the second protrusion in the second triangle member sized to be rotatably received in the first detent in the first triangle member, the first and second protrusions positioned and aligned to allow the first and second triangle members to be selectively rotated between an open position and a closed position, with the closed position enabling the back side of the first triangle member to be positioned adjacent to and parallel with the front side of the second triangle member, thereby forming a snap together pivotal assembly therebetween.

13. The food group monitoring apparatus of claim 1, wherein the acute angles formed between the left side portion, the right side portion and the base portion of the first and second triangle members are rounded to eliminate sharp corners.

14. The food group monitoring apparatus of claim 1, wherein a raised ridge portion extends at least partially along the left and right sides of one of the first and second triangle members, the raised ridge portion serving to position the triangle sheet in relation to the first and second triangle members, and further serving as a catch means to releasably secure the first and second triangle members in a closed position.

15. A food group monitoring apparatus, comprising:
   a) a first triangle member having a base portion, a left side portion, a right side portion, a front planar surface and a back planar surface;
   b) a second triangle member having a base portion, a left side portion, a right side portion, a front planar surface and a back planar surface, the second triangle member of substantially the same size as the first triangle member;
   c) a hinge means extending between the base portion of the first triangle member and the base portion of the second triangle member;
   d) a preprinted triangular sheet material sized to be received between the back surface of the first transparent triangle member and the front surface of the second triangle member when the first and second triangle members are in a closed position, the preprinted triangular sheet material having food indicia thereon representative of a plurality of food groups, the food indicia on the preprinted triangular sheet material positioned to be visible through the first triangle member;
   e) a plurality of apertures extending in complimentary alignment between the first triangle member and the second triangle member when the first and second triangle members are in said closed position, the plurality of apertures selectively positioned in alignment with food indicia representative of each of the selected food groups on the preprinted triangular sheet material, the quantity of apertures selected to be the recommended maximum quantity for consumption of each of the selected food groups over a pre-determined time period; and
   f) a flexible strap having a first end and a distal end, the first end of the flexible strap secured to one of the first triangle member, the second triangle member and the hinge means, the flexible strap sized to position the distal end of the flexible strap in alignment with any selected one of the plurality of apertures in the first triangle member; and
   g) a punch means secured in proximity to the distal end of the flexible strap; the punch means having a shaft sized to be closely received into any one of the plurality of apertures, the shaft sized to selectively punch through the first triangle member, the preprinted triangular sheet material, and at least a portion of the second triangle member; and the first triangle member, the second triangle member, the hinge means, the flexible shaft and the punch means are molded as a single unit.

16. The food group monitoring apparatus of claim 15, wherein the preprinted triangular sheet material has a front side and a back side, and the back side of each preprinted food group triangle sheet is at least partially coated with a peelable adhesive, and said preprinted triangular sheet material is placed in a book to provide a sequential history of a user's food group monitoring pattern over time.

17. The food group monitoring apparatus of claim 16, wherein adjacent preprinted triangular sheet material is releasably secured together with a peelable adhesive and placed into a substantially triangular pad for ease of handling.

18. A food group monitoring apparatus, comprising:
   a) a first triangle member having a base portion, a left side portion, a right side portion, a front planar surface and a back planar surface, the first triangle member having a base portion selected from a range of from one inch to four and one-half inches, with the left and right side portions symmetrically positioned and sized to be within plus or minus 30 percent of the length of the base portion;
   b) a second triangle member having a base portion, a left side portion, a right side portion, a front planar surface and a back planar surface, with the base portion of the second triangle member hingedly connected by a hinge means to the base portion of the first transparent triangle member;
   c) a preprinted triangular sheet material sized for insertion between the first triangle member and the second triangle member, the preprinted triangular sheet material having food indicia representative of a plurality of food groups positioned on at least one side thereon; the preprinted triangular sheet material being visible through at least one of the first and second triangle members;
   d) a plurality of apertures extending in complimentary alignment between the first triangle member and the second triangle member when the first and second triangle members are in a closed position about the hinge means, the plurality of apertures selectively positioned in alignment with indicia representative of each of selected food groups on the food triangle, the quantity of apertures in alignment with each of the food groups selected to be the recommended maximum food consumption for each food group per day;
   e) a flexible strap extending from one of the first triangle member, the second triangle member and the hinge means; the flexible strap having a distal end sized to extend substantially over any one of the plurality of apertures;

f) a punch means having a shaft secured in proximity to the distal end of the flexible strap, the punch means shaft sized to be closely received through a selected one of the plurality of apertures extending through the first and second triangle members when the first and second triangle members are in a closed position about the hinge means, the punch means shaft further having an inclined distal end for ease of penetrating through the preprinted triangle sheet material.

19. The food group monitoring apparatus of claim 18, wherein a raised ridge portion extends at least partially along at least one of the left and right sides of one of the first and second triangle members, to align the preprinted triangle sheet in relation to the first and second triangle members, and to serve as a catch to releasably retain the first and second triangle members in a closed position.

* * * * *